(12) United States Patent
Dedmon et al.

(10) Patent No.: US 11,132,922 B2
(45) Date of Patent: Sep. 28, 2021

(54) SYSTEMS AND METHODS FOR OTOLOGIC SURGICAL SKILLS TRAINING

(71) Applicant: Vanderbilt University, Nashville, TN (US)

(72) Inventors: Matthew M. Dedmon, Nashville, TN (US); Neal P. Dillon, Nashville, TN (US); Patrick S. Wellborn, Nashville, TN (US); Robert F. Labadie, Nashville, TN (US); Alejandro Rivas, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 518 days.

(21) Appl. No.: 15/963,886

(22) Filed: Apr. 26, 2018

(65) Prior Publication Data

US 2018/0315348 A1  Nov. 1, 2018

Related U.S. Application Data

(60) Provisional application No. 62/490,545, filed on Apr. 26, 2017.

(51) Int. Cl.
*G09B 23/34* (2006.01)
*G09B 23/28* (2006.01)
*A61B 1/227* (2006.01)

(52) U.S. Cl.
CPC ............ *G09B 23/34* (2013.01); *G09B 23/28* (2013.01); *A61B 1/227* (2013.01)

(58) Field of Classification Search
None
See application file for complete search history.

(56) References Cited

U.S. PATENT DOCUMENTS

| | | | | |
|---|---|---|---|---|
| 4,279,355 A | * | 7/1981 | Schwartz | B65D 50/061 215/222 |
| 6,241,526 B1 | * | 6/2001 | Auran | G09B 23/32 434/262 |

(Continued)

OTHER PUBLICATIONS

Barber et al., "3D-printed pediatric endoscopic ear surgery simulator for surgical training," Int J Pediatr Otorhinolaryngol., 2016; 90:113-118.

(Continued)

*Primary Examiner* — James B Hull
(74) *Attorney, Agent, or Firm* — Michael Best & Friedrich LLP

(57) ABSTRACT

An otologic surgical skills training method and system include a housing that receives a removably attachable simulated ear canal working port for practicing transcanal surgery skills, and a second larger working port for practicing otologic surgery skills with lower spatial constraints. The training system may be 3D printed. Dimensions of the system provide an appropriate working distance for otologic surgery simulation. Surgical instruments such as endoscopic and microscopic instruments are received via the working port to reach an otologic surgery skill exercise module. The exercise module may be attached to a platform fixed in the housing or is configured within a self-contained working port. Exercises include placing rings on pegs, stacking nuts, placing beads onto a wire, and navigating a maze with a bead, and allow for practicing with minimal depth perception, placing prostheses at a variety of angles, prostheses soft release, and instrument feel and control.

15 Claims, 15 Drawing Sheets

(56) References Cited

U.S. PATENT DOCUMENTS

2015/0037773 A1* 2/2015 Quirarte Catano .... G09B 23/30 434/262
2017/0061827 A1* 3/2017 Sherman ................ G09B 23/28

OTHER PUBLICATIONS

Clark et al., "Development and validation of a low-cost microsurgery Ear Trainer for low-resource settings," J Laryngol Otol., 2016; 130(10):954-961.

Dedmon et al., "Development and validation of a modular endoscopic ear surgery skills trainer," Otol Neurotol., 2017; 38:1193-1197.

Monafared et al., "High-fidelity, inexpensive surgical middle ear simulator," Otol Neurotol., 2012; 33(9):1573-1577.

Brunt, "Celebrating a decade of innovation in surgical education," Bull. Am. Coll. Surg., 2014; 99(11):10-15.

Dedmon et al., "Development of a Temporal Bone Model for Transcanal Endoscopic Ear Surgery," Otolaryngol. Head Neck Surg., 2015; 153(4):613-615.

Ericsson et al., "Expert and exceptional performance: Evidence of maximal adaptation to task constraints," Annu. Rev. Psychol. 1996; 47:273-305.

Gibbs et al., "Learning Curves for New Procedures—The Case of Laparoscopic Cholecystectomy," Making Health Care Safer: A Critical Analysis of Patient Safety Practices, Agency Healthc. Res. Qual., 2001; 213-220.

Nagendran et al., "Cochrane Database of Systematic Reviews," ed. The Cochrane Collaboration, John Wiley & Sons, Ltd, 2013; 1-43.

Palter et al., "Individualized Deliberate Practice on a Virtual Reality Simulator Improves Technical Performance of Surgical Novices in the Operating Room: A Randomized Controlled Trial," Ann. Surg. 2014; 259:443-448.

Stankiewicz, "Complications in endoscopic intranasal ethmoidectomy: an update," The Laryngoscope, 1989; 99:686-690.

Tarabichi et al., "Transcanal endoscopic management of cholesteatoma," Otolaryngol. Clin. North Am., 2013; 46:107-130.

Tarabichi, "Endoscopic middle ear surgery," Ann. Otol. Rhinol. Laryngol., 1999; 108; 39-46.

* cited by examiner

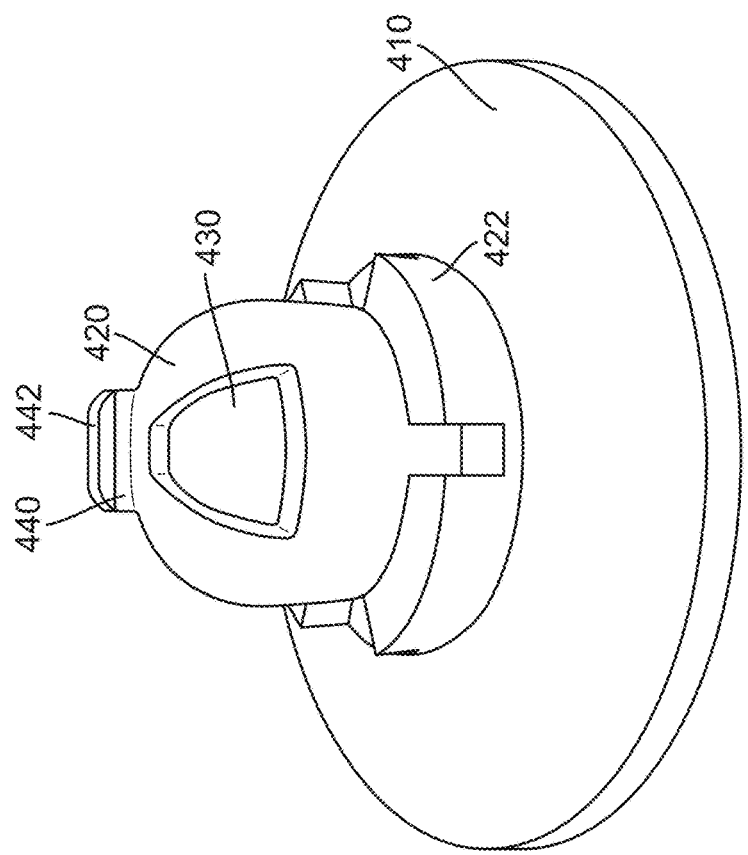
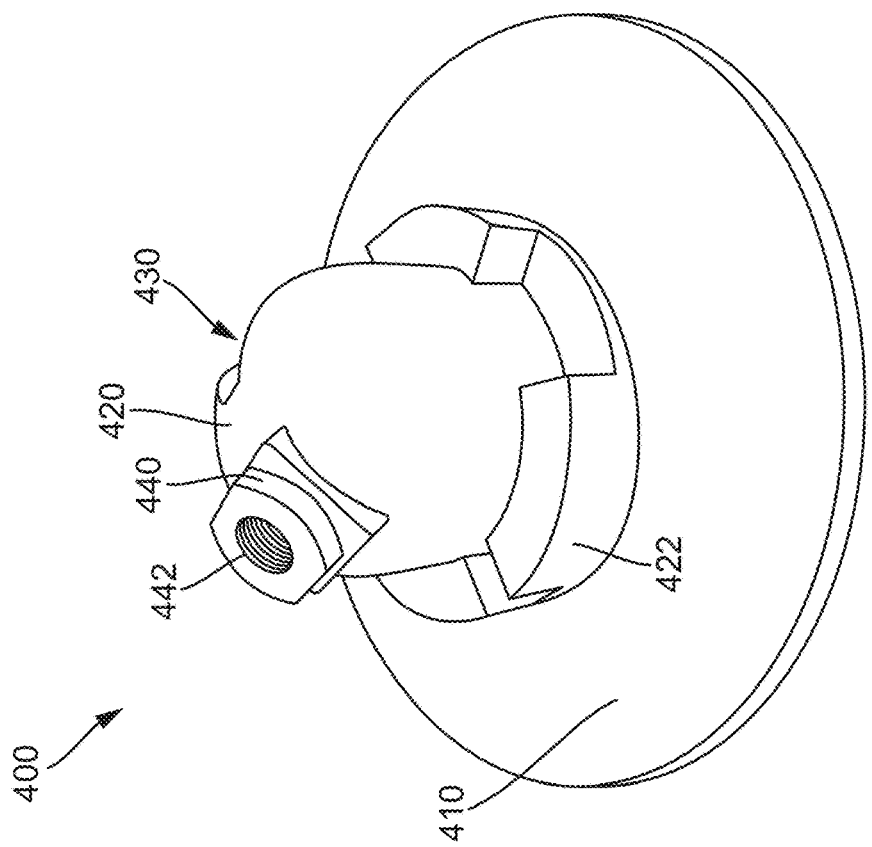

SYSTEMS AND METHODS FOR OTOLOGIC SURGICAL SKILLS TRAINING

CROSS-REFERENCE TO RELATED APPLICATIONS

This application is a non-provisional of and claims the benefit of U.S. Provisional Patent Application Ser. No. 62/490,545, filed on Apr. 26, 2017, the entire contents of which are incorporated herein by reference.

TECHNICAL FIELD

The invention relates to methods and systems for otologic surgical skills training. More specifically the invention relates to an otologic surgery skills training device used to teach and practice technical skills using multiple exercises related to both microscopic and endoscopic ear surgery.

BACKGROUND OF THE INVENTION

The hallmark of surgical training for the past century has been the Halstedian concept of apprenticeship. The foundation for this model rests on the acquisition of experience via the completion of a prodigious number of cases, yet increasing clinical pressures and shorter working schedules have left current trainees with fewer operating hours than ever before. Surgical simulation may provide a solution to this problem by enabling the development of critical skills in a controlled environment. The potential benefits of learning surgical techniques without endangering patients in real operating scenarios are immense, and many institutions have incorporated surgical skills centers as key components of surgeon training. Moreover, studies suggest that skills learned in a simulated environment can improve performance in real operating scenarios.

Expert performance in athletics and music has been correlated with participation in repetitive, deliberate practice. Surgical performance is also likely to benefit from deliberate practice, particularly in specialties like ear surgery, which requires precise motor control with movements on the sub-millimeter scale under high magnification. The current otologic surgical training paradigm includes occasional drilling practice using expensive cadaveric temporal bones; however, essentially all learning of middle ear dissection and instrument techniques, which include some of the most delicate and difficult components of ear surgery, occurs on real patients.

Ear surgery techniques traditionally use a microscope for visualization of the tympanic membrane and middle ear structures, and microscopic surgery is a standard component of all otolaryngology training programs. Therefore, a skills trainer that enables practice of microscopic techniques would be exceedingly useful. In addition, the quest for minimally-invasive surgical approaches has resulted in a novel technique that uses a rigid endoscope in the ear canal for visualization rather than a microscope. The endoscopic approach provides a much wider view of the middle ear, and allows clear visualization of spaces that are typically hidden from microscopic view. These hidden spaces may contain diseased tissue that must be removed to prevent recurrence, and would be otherwise missed when using a microscope if extensive drilling of bone is not performed. In addition, the use of the endoscope can frequently eliminate the need for a large incision and dissection behind the ear, instead requiring only a small incision in the ear canal to perform the entire procedure. However, endoscopic ear surgery is a very challenging technique even for the most accomplished otologist, requiring one-handed dissection using angled endoscopes and instruments with minimal depth perception. It has been shown that the prior introduction of new, challenging techniques such as endoscopic sinus surgery and laparoscopic surgery was associated with a rise in patient complications as inexperienced surgeons began adopting the techniques. With interest in endoscopic ear surgery continuing to grow, it is imperative that there is a way to teach and practice this technique in order to minimize surgical complications and improve patient outcomes, and a surgical skills trainer could play a key role in adoption of this new technique.

Previously developed techniques include a cadaveric temporal bone model for endoscopic dissection of cholesteatoma, which is a destructive skin lesion of the middle ear and mastoid, but this model is difficult to produce in a standardized fashion and has limited versatility. The teaching of laparoscopic surgery is based on the Fundamentals of Laparoscopic Surgery (FLS) program. This program includes a didactic portion along with skills exercises on a simulator. These exercises consist of simple tasks such as transferring pieces of foam to pegs using two hands, and cutting out a paper circle with laparoscopic instruments using a skills trainer box. These exercises were vetted by experts and extensively validated. Since its inception more than 10 years ago, over 9,000 surgeons have completed the training. Repetitively practicing ear surgery techniques in a safe environment could accelerate skill acquisition, enhancing the overall training of otologic surgeons as well as improving patient care. A formal skills training program for microscopic and endoscopic ear surgery would be extremely useful in shortening the learning curve and reducing surgical complications.

SUMMARY OF THE INVENTION

Ear surgery training programs include laboratory temporal bone drilling sessions, but there are currently no easy, safe ways to practice microscopic and endoscopic middle ear dissection techniques. Therefore, the majority of technique acquisition and refinement is acquired during real cases in the operating room. However, technical ear surgery skills could be taught and practiced in a safe environment using a surgical skills trainer. The advantages include low cost compared to purchasing cadaveric temporal bones, and the ability to repetitively practice key skills in a standardized fashion outside the operating room. The system includes a surgical skills trainer complete with a range of instrument entry ports and individual skills modules that allow practice of both microscopic and endoscopic ear surgery techniques. These exercises will facilitate the acquisition of basic techniques such as instrument control, precision movements, and operating with limited depth perception in the case of endoscopic ear surgery. This device could be a component of ear surgery training in every otolaryngology residency program worldwide, and could also be used to demonstrate products such as middle ear prostheses and tympanic membrane repair grafts at courses and conferences.

In some embodiments, the invention provides a system for otologic surgical skills training that includes an outer housing and a working port in the outer housing. The working port is configured to receive a removably attachable simulated ear canal working port. The removably attachable simulated ear canal working port is configured to receive an otologic surgical instrument for performing otologic surgery exercises on an otologic surgery skill exercise module.

In some embodiments, the invention provides a method for otologic surgical skills training that includes receiving, by a working port in an outer housing of an otologic surgical skills training device, a removably attachable simulated ear canal working port. The removably attachable simulated ear canal working port is configured to receive an otologic surgical instrument for performing otologic surgery exercises on an otologic surgery skill exercise module.

In some embodiments, an otologic surgical skills training device includes a housing and a self-contained ear canal simulation port attached to the housing. The self-contained ear canal simulation port is configured to receive an otologic surgical instrument for performing otologic surgery exercises within the self-contained ear canal simulation port. The self-contained ear canal simulation port comprises components configured for manipulation by the otologic surgical instrument and reachable by the otologic surgical instrument via the ear canal simulation port for the performance of the otologic surgery exercises within the self-contained ear canal simulation port.

In some embodiments, a system for otologic surgical skills training includes a housing with an ear canal simulation port in the housing. The ear canal simulation port is configured to receive an otologic surgical instrument for performing otologic surgery exercises within the housing via the ear canal simulation port. A skill module within the housing is configured with components for manipulation by the otologic surgical instrument and reachable by the otologic surgical instrument via the ear canal simulation port for the performance of the otologic surgery exercises.

In some embodiments, a system for otologic surgical skills training includes a top housing comprising a removably attachable port and a bottom housing removably attachable to the top housing. A skill module is removably attachable within the bottom housing and reachable by an otologic surgical instrument via the removably attachable port. Components of the skill module are configured for manipulation by the otologic surgical instrument. The removably attachable port is configured to receive the otologic surgical instrument for otologic surgery exercises via the removably attachable port.

Other aspects of the invention will become apparent by consideration of the detailed description and accompanying drawings.

BRIEF DESCRIPTION OF THE DRAWINGS

FIGS. 4A-4E illustrate an exemplary 3D printed otologic surgery training system, according to some embodiments.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Systems and methods are provided for a versatile surgical skills trainer that can facilitate the acquisition of key microscopic and endoscopic ear surgery skills in a safe environment. The surgical skills trainer provides an inexpensive, standardized, reproducible device that supports validated exercises and easy assessments. The easily reproducible modular device may become a key component of ear surgery training programs worldwide, and ultimately accelerate skill acquisition and improve surgical performance.

Embodiments of the invention include a modular ear surgery skills trainer used to teach and practice technical skills related to both microscopic and endoscopic ear surgery. It comprises a platform with an outer housing that provides a large working port for instrument passage, as well as a circular port that allows simulation of ear canals of varying diameters through which the exercises can be performed. Some individual skills modules include transferring rings to pegs, placing beads onto thin wires, and navigating a maze with a bead. A handmade trainer was developed for initial testing. The ear surgical skills trainer may also be produced by large-scale 3D printing based on a computer model of the trainer. Applications for this device include use in otolaryngology training programs worldwide, as well as for demonstration of skills and reconstructive materials at educational conferences and courses.

Figure 1A:
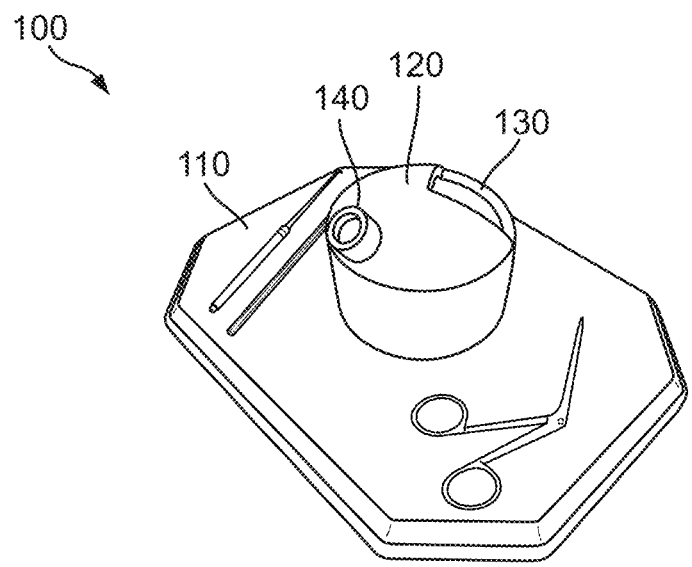
FIGS. 1A-1B illustrate a perspective view and a rear view of an exemplary otologic surgery training system, according to some embodiments.
Figure 1B:
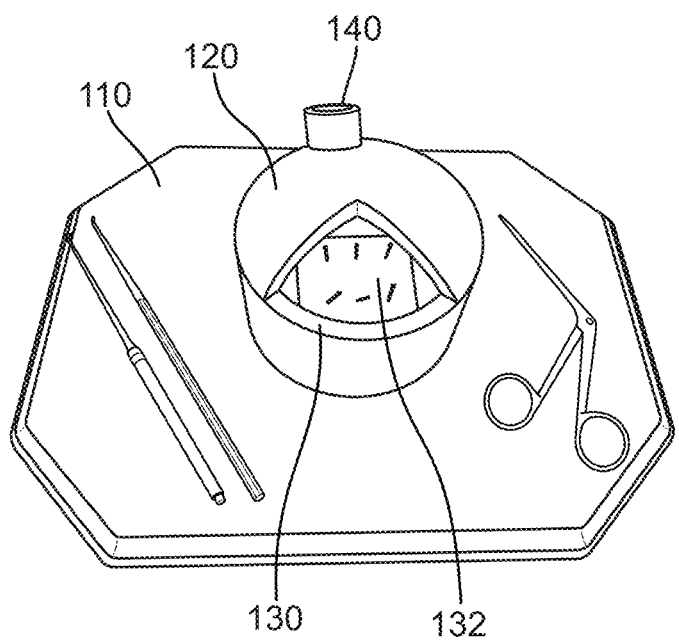
Figure 2A:
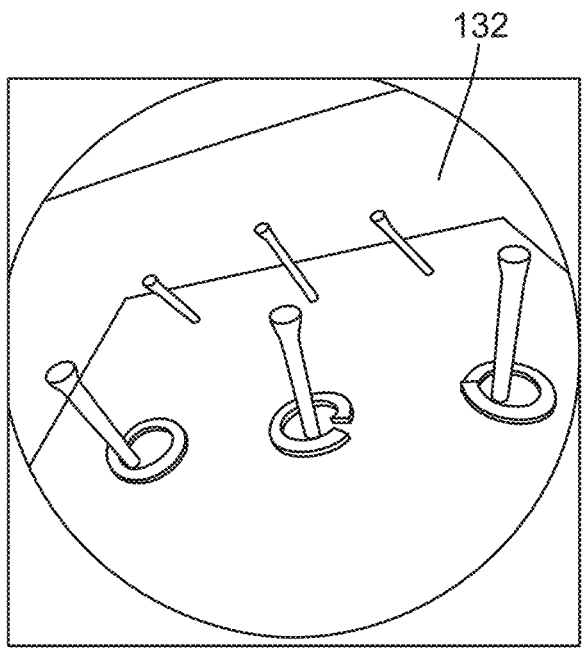
FIGS. 2A-2H illustrate a variety of exemplary surgery skill exercise modules for use in an otologic surgery training system, according to some embodiments.
Figure 2B:
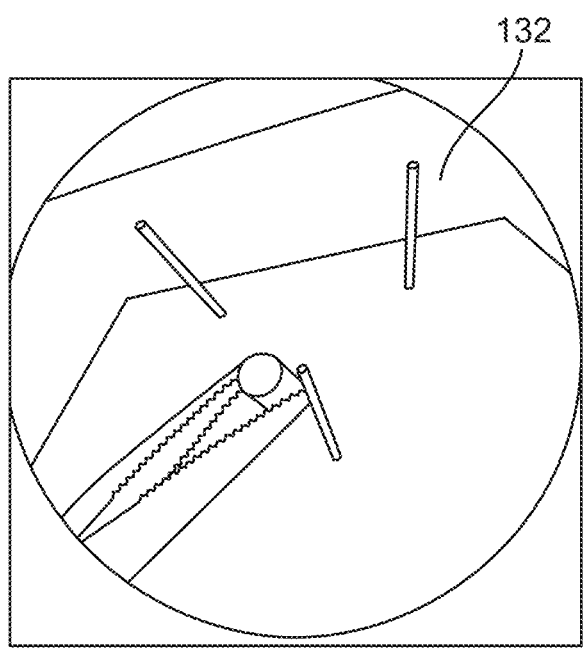
Figure 2C:
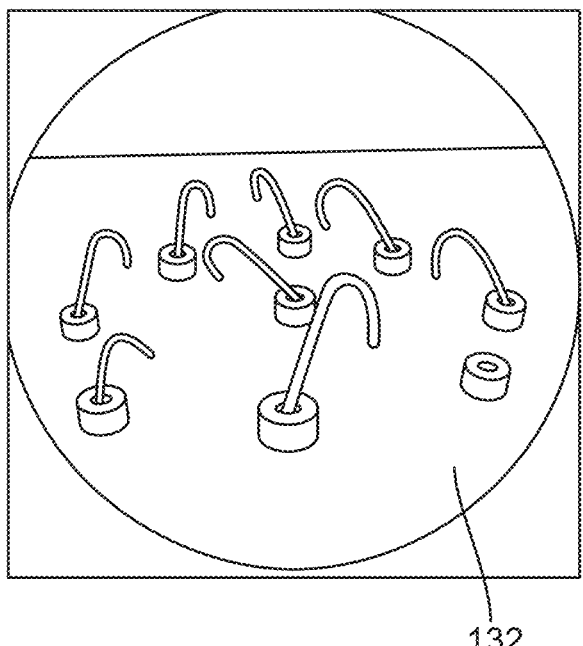
Figure 2D:
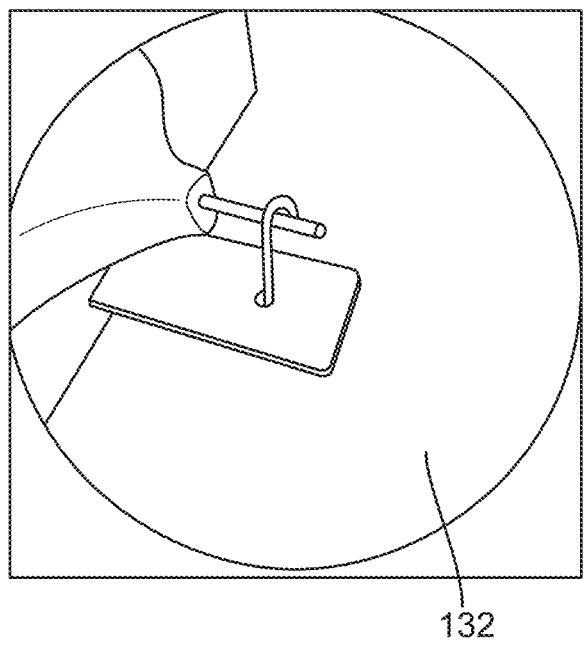
Figure 2E:
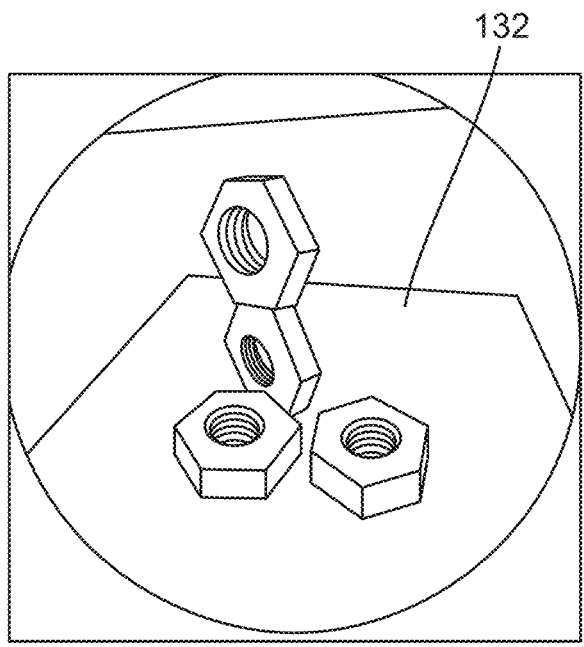
Figure 2F:
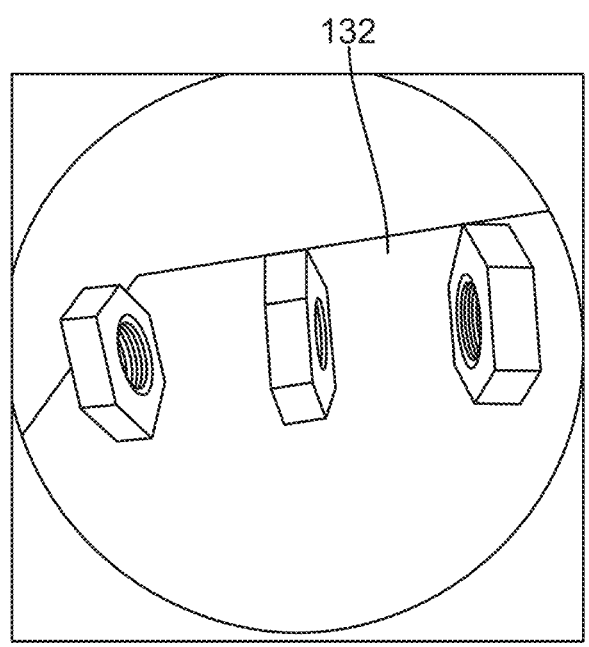
Figure 2G:
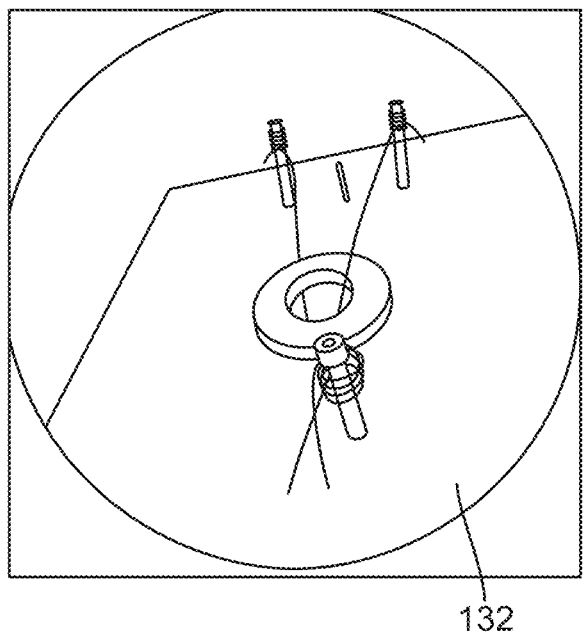
Figure 2H:
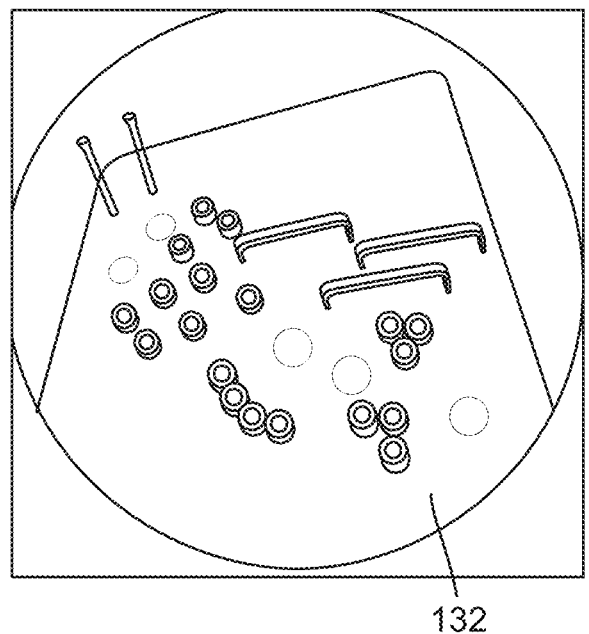

FIGS. 1A-1B illustrate a perspective view and rear view of an exemplary otologic surgery training system, according to some embodiments. Shown in FIGS. 1A-1B is an otologic surgery training system 100 that includes a base 110, a training device housing 120, an otologic surgery skill exercise module 132, a large working port 130, and a small working port 140. The small working port 140 may be referred to as a transcanal working port or simulated ear canal working port. The otologic surgery skill exercise module 132 may be referred to as an exercise module, skills module or cartridge.

In some embodiments, the training device housing 120 may be fixed to the base 110. The training device housing 120 has a curved top surface and sidewalls, and is scaled to provide an environment for simulating otologic surgery conditions for example transcanal surgery utilizing various surgical instruments including endoscopic and microscopic instruments and forceps. A platform (not shown) placed within an interior volume of the housing 120 supports the exercise module 132 (see examples of exercise modules in FIGS. 2A-2H). The platform is disposed or fixed to the interior of the training device housing 120 at an appropriate distance from the top of the small working port 140 for simulating ear surgery on components of the exercise module 132. This distance may be referred to as a working distance. One example working distance for ear surgery of approximately 3 cm correlates to the distance from the external auditory canal meatus to the middle ear.

The training device housing 120 includes two working ports for inserting surgical instruments and practicing otologic surgery techniques at an appropriate working distance. These working ports are referred to as small and large. The small working port has a diameter dimension that is smaller than the large working port and vice versa. The small working port 140 simulates an ear canal in that the diameter of the port provides spatial constraints encountered during actual transcanal ear surgery on a patient. The large working port 130 provides greater spatial dimensions for passage of instruments into the interior of the training device housing to the exercise module 132. The large working port enables users to improve skills while having space for a greater range of motion and also for practicing skills for ear surgeries performed via larger openings made behind the ear. Although a prototype of the training device housing 120 is made with a three inch PVC pipe cap modified (top surface) with a cylinder providing the small working port 140, and an opening for the second larger port 130, the training device 120 is not limited to any specific types of materials or methods of construction or manufacture. For example, an otologic surgery skills training system 100 may be manufactured with interchangeable parts for large scale reproduction utilizing 3D printing or other methods. The otologic surgery skills training system 100 provides a versatile platform for performing otologic surgery exercises including transcanal endoscopic and microscopic ear surgery.

The small working port 140 and large working port 130 provide an instrument passageway to an environment within the interior of the housing 120 for performing otologic surgery skill improvement exercises on the skill exercise module 132. The small working port 140 allows a user to practice transcanal otologic surgical techniques under dimensional constraints such as those experienced when working on a patient. In some embodiments the small working port is circular and may be referred to as the circular working port. The depth of the skill exercise module 132 relative to the top of the small port 140 is based on anatomical dimensions so as to provide a realistic hand to surgical subject working distance for otologic surgery including transcanal endoscopic and microscopic ear surgery. For example, the depth may be based on a pediatric anatomy or an adult anatomy and the dimension of instruments handled by a user to reach the exercise module 132. Furthermore, diameter and/or volumetric shape of the small working port 140 may be based on anatomical dimensions that simulate an ear canal. In this regard, the small working port 140 provides realistic working dimensions for inserting instruments utilized in otologic surgery and reaching features of interest in the interior of an ear.

FIGS. 2A-2H illustrate a variety of exemplary surgery skill exercise modules for use in an otologic surgery training device, according to some embodiments. Additional examples are described with respect to FIGS. 3 and 4A-4F.

FIGS. 2A-2H include eight examples of a skill exercise module 132 that are designed to improve handling of a variety of surgical instruments including microscopic and endoscopic instruments and develop proficiency in certain surgical techniques. Exercises performed with the skill exercise modules 132 facilitate the acquisition of basic techniques such as instrument control, precision movements, fine motions under high magnification, and operating with minimal depth perception using a video screen. The scale and design of components of the exercise modules 132 allow users to work on structures having a sub-centimeter or sub-millimeter scale. The example skill modules 132 shown in FIGS. 2A-2H are prototypes constructed of wooden squares (approximately 3 cm×3 cm) using materials such as #19 wire brads, 1.6 mm glass beads, and 26-gauge jewelry wire for the module's manipulated components. These modules provide for exercises such as placing rings on pegs, stacking nuts, placing beads onto a wire, or navigating a maze with a bead. A thread the needle exercise allows practice of precisely placing beads while working with minimal depth perception. Reverse thread the needle exercises allow practice of placing simulated prostheses into beads at a variety of angles and distances. Use of these skills modules 132 requires a high level of instrument control, soft release of the prostheses, as well as optimization of the endoscopic or microscopic view. Some exercise modules are designed for replication of a specific procedural component such as stapes prosthesis placement (FIG. 2D), while others such as "Spin the Wheel" (FIG. 2F) were not based on specific movements, but rather designed to enhance feel and instrument control. Although the examples shown in FIG. 2A-2H are constructed by hand, using wood and off the shelf hardware, a skill exercise module 132 is not limited to any specific types of materials or methods of construction. For example, skill exercise modules 132 and/or the module components may be manufactured wholly or in part by mass production means, for example, utilizing 3D printing or by other manufacturing methods. In one example, a portion or a base of a skills exercise module 132 is configured for mass production and additional parts, such as pegs or wires may be hand or machine assembled onto the base. A 3D printed skills exercise module 132 base may be mass produced and configured with holes, protrusions, ridges and/or grooves of various shapes and sizes for attaching or connecting separate parts of the exercise modules.

Figure 3:
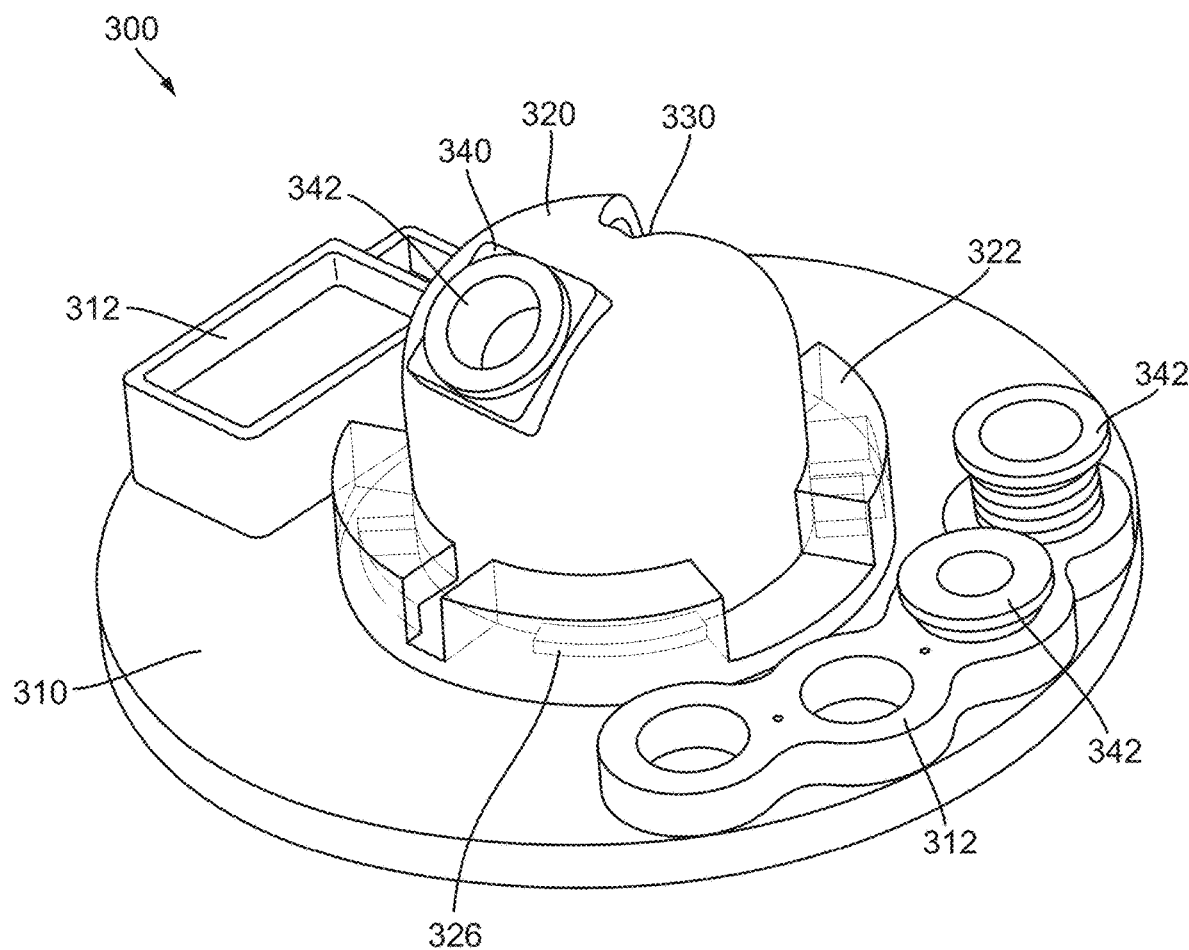
FIG. 3 illustrates an exemplary 3 dimensional (3D) computer model for manufacturing an otologic surgery training system, according to some embodiments.

FIG. 3 illustrates an example of a 3-dimensional (3D) computer model for manufacturing an otologic surgery training system, according to some embodiments. Shown in FIG. 3 is an otologic surgery training system computer model 300 that includes a top housing 320, a large working port 330, a small working port 340, a simulated ear canal working port attachment 342, a bottom housing 322, a locking mechanism 326, and a base 310. The otologic surgery training system computer model 300 may be referred to as the computer model 300. A platform for fixing an otologic surgery skill exercise module attachment, and exercise module components are not shown in FIG. 3 (see FIGS. 2A-2H, 4C, and 4D). The simulated ear canal working port attachment 342 may be referred to as an insert.

The computer model 300 is based, in part, on the otologic surgery training system 100 and may be utilized for manufacturing an otologic surgery training system. In some embodiments, 3D printing methods may be utilized for manufacturing an otologic surgery training system based on the computer model 300 or other model configurations. Moreover, all or portions of the otologic surgery training system 100 as well as additional features described herein may be mass produced using a 3D printing process or other forms of large-scale reproduction. The computer model 300 may include a life-size otologic surgery environment with appropriate working distances for users practicing surgical skills.

In some embodiments, the computer model 300 includes the top housing 320 having a curved top surface and sidewalls forming a cylinder. However, the top housing is not limited to a specific geometry and any geometry suitable for manufacturing processes such as 3D printing reproduction may be utilized. An open window section in the top housing 320 comprises the large working port 330 for instrument passage into the interior of the top housing 320 for access to an otologic surgery skill exercise module (not shown) that is disposed or fixed within the bottom housing 322. In some embodiments, the scale of the large working port 330 may include approximately a quarter or third of the circumference of the top housing and extend vertically into the curved top surface from the cylindrical sidewall. However, the disclosure is not limited to any specific dimensions or shape for the large working port 330. The large working port 330 may be suitably configured for passing otologic surgical instruments including an endoscope or microscope into the outer housing for surgery exercises.

The small working port 340 comprises an opening in the top housing 320 that extends into the interior of the top housing 320. In some embodiments the small working port may be circular or other shapes, and may be referred to as a circular working port. The small working port 340 allows access to an otologic surgery skill exercise module (not shown) disposed or fixed in the bottom housing 322. In some embodiments, the inner circumference of the small working port 340 may have dimensions on the order of an ear canal. However, in some embodiments, the small working port 340 is configured to receive a variety of different types of simulated ear canal working port attachments 342. For example, the small working port 340 may be configured to detachably fix a simulated ear canal attachment 342 that is inserted into the small working port 340. In one embodiment the small working port 340 may be threaded to engage threading on a simulated ear canal port attachment 342. However, the disclosure is not limited in this regard and mechanisms other than threading or different configurations may be utilized to secure or fix a simulated ear canal attachment to the top housing 320.

The simulated ear canal working port attachment 342 may extend inward towards the otologic surgery skill exercise module (not shown) disposed or fixed within the bottom housing 322. In some embodiments, a variety of simulated ear canal port attachments 342 may have different dimensions based on different anatomical data for different types of patients and/or different pathologies. For example, the simulated ear canal working port attachments may come in varying diameters such as large medium and small that allow increasing difficulty in performing otologic surgery exercises. The simulated ear canal working port attachments 342 may be reusable and interchangeable within the small working port 340. Alternatively the working port attachments 342 may be disposable inserts. In some embodiments, the simulated ear canal working port attachment 342 may not be a removable component and instead may be permanently fixed to the top housing 320. Simulated ear canal working port attachments 342 may have various levels of fidelity with respect to the anatomy of an external auditory canal and/or middle ear. For example, the attachments 342 may range from having simple shapes such as a cylinder with dimensions that are useful for practicing transcanal ear surgery to having varied physical dimensions and/or characteristics based on detailed anatomical data such as for the external auditory canal and/or middle ear. Simulated ear canal working port attachments 342 may also be closed or self-contained such that instruments to not reach into a separate exercise module disposed in the bottom housing 322 instead reach features within the working port attachment 342 for surgery skills exercises.

The bottom housing 322 is configured to removably receive the top housing 320 such that a user can gain access to the interior of the trainer 300 housing. In one example, the bottom housing 322 has a cylindrical sidewall with an open top. The interior diameter of cylindrical sidewall of the bottom housing is large enough to receive the top housing 320 within its interior perimeter. The top housing 320 and bottom housing 322 may be configured with a locking mechanism to secure the top and bottom housings together. In one example, a rotating locking mechanism 326 includes one or more tab extensions radiating outward from the bottom of the top housing 320. The tab extensions are received in a downward vertical direction by corresponding cutout sections in the cylindrical sidewall of the bottom housing 322. When the top housing 320 is received by the bottom housing 322 and rotated relative to the bottom housing, the tab extensions slide into horizontal grooves in the interior of the cylindrical sidewall of the bottom housing 322 to lock the top housing 320 to the bottom housing 322. The rotating locking mechanism 326 allows for easy removal of the top housing 320 to change otologic surgery skill exercise module attachments in the bottom housing 322. However, the otologic surgery training system or the model 300 is not limited to any specific type of locking mechanism and any attachment mechanism for attaching the top housing 320 to the bottom housing 322 may be utilized.

Figure 4D:
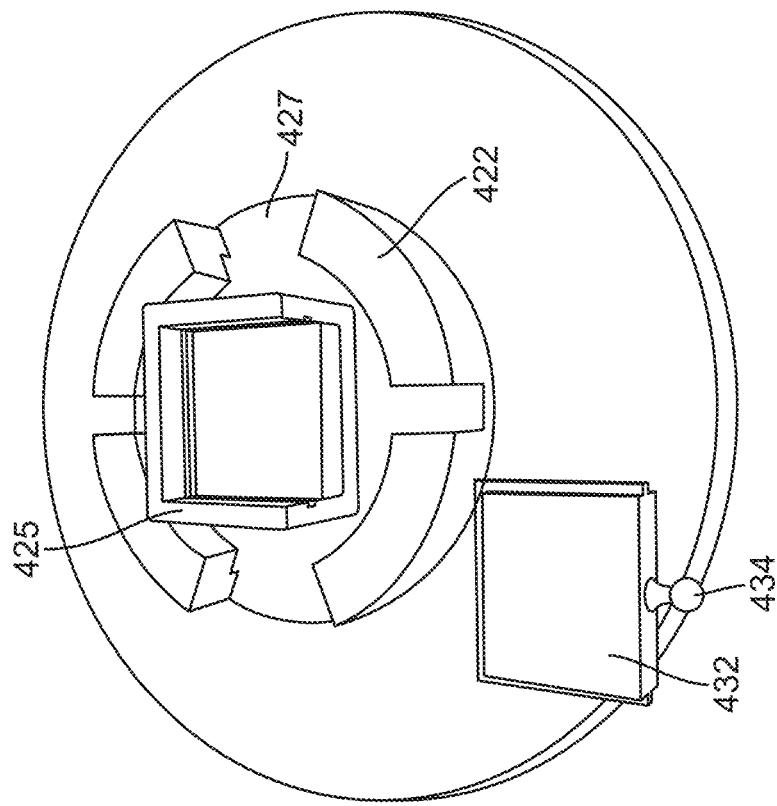
Figure 4C:
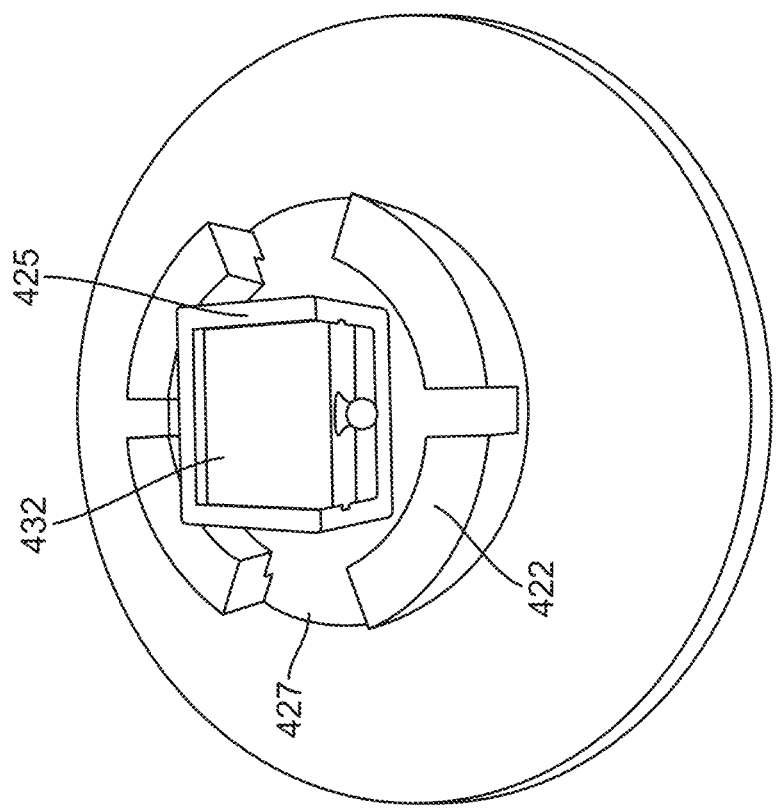
Figure 4E:
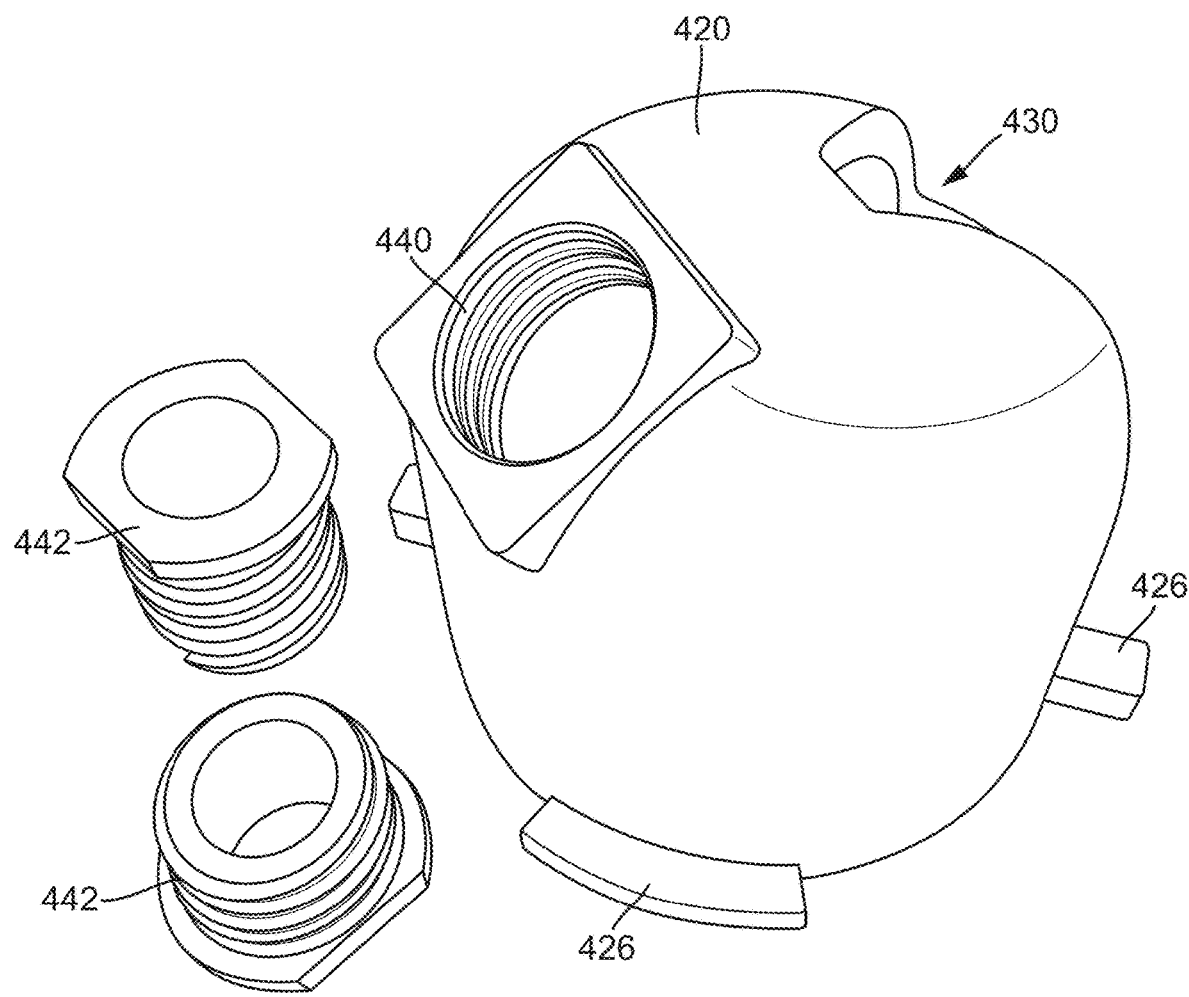

In some embodiments, the bottom housing 322 includes a fixed platform for receiving removable otologic surgery skill exercise module attachments (see FIGS. 4C and 4D). For example, the fixed platform may include a slot or groove for receiving interchangeable skill exercise module attachments that may be similar to the exercise modules 126. The fixed platform and the skill exercise module attachments may be connected by a sliding mechanism to secure the exercise modules to the fixed platform in the bottom housing 322.

In some embodiments, the bottom housing 322 includes a base 310. For example, the bottom housing 322 and the base 310 may be manufactured as a single piece. Alternatively, the bottom housing 322 may be a standalone housing piece without the base 310 or may be attached or removably attached to the base 310. In some embodiments, the base 310 is configured with compartments or structures 312 to hold removable parts of the otologic surgery training system or instruments utilized during otologic surgery exercises. For example, the base 310 may be configured with compartments or structures 312 to hold a variety of simulated ear canal attachments 342 that may have varying internal sizes and shapes. The base 310 may also be configured with compartments or structures 312 to hold a variety of interchangeable or disposable surgical skill exercise modules for practicing different otologic surgical skills such as instrument handling, use of angled endoscopes, single-handed dissection techniques, working with non-dominant hand, precision movements, working with limited depth perception, and specific surgical moves.

An otologic surgery training system may be manufactured including the features described with respect to the computer model 300.

FIGS. 4A-4E illustrate an example of a 3D printed otologic surgery training system, according to some embodiments. Shown in FIGS. 4A-4E is a 3D printed otologic surgery training system 400 that includes a base 410, a top housing 420, a large working port 430, a small working port 440, a simulated ear canal working port attachment 442, a bottom housing 422, a platform 425, a locking mechanism tab and/or rail 426, a locking mechanism cutout 427, and an otologic surgery skill exercise module attachment 432. The otologic surgery skill exercise module attachment 432 may be referred to as a cartridge.

The 3D printed otologic surgery training system 400 is an example of a system that is 3D printed based on a computer model such as the computer model 300, and includes features described with respect to FIGS. 1A-1B, 2A-2H and 3. The otologic surgery training system 400 may be 3D-printed using a plastic material such as a thermoplastic polymer. For example, acrylonitrile butadiene styrene (ABS) may be used. The otologic surgery training system 400 is easily reproducible for mass production.

The otologic surgery training system 400 includes an outer housing. In some embodiments the outer housing includes the top housing 420 having a curved top surface and sidewall. However, the disclosure is not limited to a specific geometry for the top housing. An open window section in the top housing 420 comprises the large working port 430 for instrument passage into the interior of the top housing 420, for example, for access to an otologic surgery skill exercise module attachment 432 disposed within the bottom housing 422. The exercise module attachment 432 may include a tab or handle 434 for maneuvering a base of the exercise module attachment 432. The scale and configuration of the large working port 430 is based on that of the working port 330 of the computer model 300.

Although the base 410 is shown as a flat surface for receiving the bottom housing 422, the base 410 may include a configuration and/or features described with respect to the base 310. In some embodiments, the bottom housing 422 includes the base 410 such that the base 410 and the bottom housing 422 are manufactured as a single part. Alternatively, the bottom housing 422 may be a standalone housing piece without the base 410 or may be attached or removably attached to the base 410. In some embodiments, the base 410 is configured with compartments or structures to hold removable parts of the otologic surgery training system 400 or instruments utilized during otologic surgery exercises. For example, the base 410 may be configured with compartments or structures 312 to hold a variety of simulated ear canal attachments 442 that may have varying internal sizes and shapes. The base 410 may also be configured with compartments or structures 312 to hold a variety of interchangeable or disposable surgical skill exercise modules 432 for practicing different otologic surgical skills such as instrument handling, use of angled endoscopes, single-handed dissection techniques, working with non-dominant hand, precision movements, working with limited depth perception, and specific surgical moves.

The small working port 440 comprises an opening in the top housing 420. In some embodiments the small working port 440 extends into the interior of the top housing 420 for passage of otologic surgical instruments. For example, the small working port 440 allows access to the otologic surgery skill exercise module attachment 432 attached to the platform 425 fixed in the bottom housing 422. The dimensions and configuration of the small working port 440 are based on the small working port 140 of FIGS. 1A-1B or 340 of the computer model 300. In some embodiments the small working port 440 is configured to receive the simulated ear canal working port attachment 442. The small working port 440 and the simulated ear canal working port attachment 442 are configured to lock or fix the working port attachment 442 to the top housing 420. For example, the small working port 440 may include threading to engage threading on the simulated ear canal attachment 442 for fixing the working port attachment 442 to the small working port 440. However, the disclosure is not limited in this regard and mechanisms other than threading, or different configurations may be utilized to secure a simulated ear canal working port attachment 442 to the top housing 420. The simulated ear canal attachments 442 may be an interchangeable module that allows for inserting different simulated ear canal working port attachments 442 having different properties into the small working port 440. For example, the different working port attachments 442 may have different diameters and/or different interior characteristics through which surgical exercises can be performed. Some simulated ear canal working port attachments 442 have dimensions based on anatomical data for different types of patients, such as adults or pediatric patients. The simulated ear canal attachment 442 may extend inward towards the otologic surgery skill exercise module attachment 432 disposed within the bottom housing 422. In some embodiments, the simulated ear canal attachments 442 may be disposable insert modules.

In some embodiments, the simulated ear canal attachments 442 may be stand-alone self-contained modules that are configured to insert into the small working port 440 of the top housing 420. These stand-alone self-contained simulated ear canal attachments 442 may include an internal surgery skills exercise module for practicing otologic surgical skills, and may not open to other interior spaces of the upper and lower housings or to the exercise module 432. The stand-alone exercise modules 442 may be utilized for, among other things, practicing surgical skills for middle ear dissection, tympanoplasty, ossicular chain reconstruction, and stapes prosthesis placement. They may be configured to hold a liquid to simulate realistic conditions that occur during surgeries and may include features that enable exercises similar those provided on the exercise module 432.

The bottom housing 422 is configured to removably receive the top housing 420. The bottom housing 422 may have a cylindrical sidewall with an open top. The interior diameter of cylindrical sidewall is large enough to receive the top housing 420 within its interior perimeter. A locking mechanism includes one or more tab and or rail extensions 426 radiating outward from the bottom of the top housing 420. The tab and/or rail extensions 426 are received in downward a vertical direction by corresponding cutout sections 427 in the cylindrical sidewall of the bottom housing 322. When the top housing 420 is received by the bottom housing 422 and rotated relative to the bottom housing, the tab and/or rail extensions 426 slide into horizontal grooves (not shown) in the interior of the cylindrical sidewall of the bottom housing 422 to lock the top housing 420 to the bottom housing 422. Other types of locking or attachment mechanisms may be utilized in an otologic surgery skills system.

In some embodiments, the bottom housing 422 includes a fixed platform 425 for holding or fixing the surgery skills exercise module 432. For example, the fixed platform 425 may be configured for slidably attaching or removing the otologic surgery skill exercise module attachment 432. The fixed platform 425 receives the exercise module attachment 432 by sliding a ridge on the perimeter of the exercise module attachment 432 into the slots or grooves of the fixed platform 425 of the bottom housing 422. However, the disclosure is not limited to any specific type of mechanism for attaching the exercise module attachment 432 to the bottom housing 422 and any suitable attachment mechanism may be utilized. For example the module may snap into place. The otologic surgery training system 400 may include multiple interchangeable otologic surgery skill exercise module attachments 432 that are based on, or may be similar to the exercise modules 132 and those described with respect to FIG. 3. As noted with respect to the skills exercise modules 132 and those described with respect to FIG. 3, the interchangeable exercise modules attachments 432 are configured for practicing different otologic surgical skills. For example, instrument handling, use of angled endoscopes, single-handed dissection techniques, working with non-dominant hand, precision movements, working with limited depth perception, and specific surgical moves may be practiced using the exercise module 432.

The otologic surgery skill exercise modules 432 and/or components of the module 432 may be may be manufactured wholly or in part by mass production means, for example, utilizing 3D printing or by other manufacturing methods. In one example, a base of a skills exercise module 432 may be configured for mass production and additional parts, such as pegs, wires, screws, nuts or similar components of any suitable material may be hand or machine assembled onto the base. A 3D printed skills exercise module 132 base may be mass produced and configured with holes, protrusions, ridges and/or grooves of various shapes and sizes for attaching or connecting the additional parts of the exercise modules. Movable, fixed, separate and/or removable components of the skill exercise module attachment 432 may be manipulated by a user with otologic surgical instruments such as an endoscope or microscopic device. Some examples of otologic surgery skill exercise module attachments 432 configurations and practice techniques include:

A pegs and rings module that is configured for a user to pick up a ring, for example, a small metal washer and transfer it to and from a series of plastic or metal pegs using a forceps.

A thread the needle module is configured for a user to pick up a bead, for example, a glass bead and slides it onto a series of wires or pegs that have been fixed to the exercise module 432 base.

A reverse thread the needle module is configured for a user to take a small cylinder, such as a metal cylinder and place it into a hole in the base of the exercise module or into the center of a bead fixed to the exercise module.

A stapes trainer module is configured for a user to place simulated or real stapes prosthesis into a hole in the exercise module 432 while simultaneously hooking it around a cylinder simulating the incus (one of the hearing bones).

A precision stacking module is configured for a user to pick up and stack rings, such as hexagonal nuts on top of each other, attempting to get the highest stack possible without tipping over.

A spin the wheel module is configured for a user to spin the rings, such as hexagonal nuts in place resting on top of the exercise module 432 base.

A split the difference module is configured for a user to push a ring, for example, a metal washer along two diverging wires for as long as possible, until the washer falls off A hypnotic module is configured for a user to push a bead, such as a glass bead along a pattern drawn or printed on the exercise module 432 base, trying to keep the bead on the line of the pattern.

A maze module is configured for a user to push a bead, such as a glass bead through a maze consisting of obstacles and/or holes, trying to get to the other side of the maze without hitting the obstacles.

A mount Midoriyama module is configured for a user to push a ring, such as a hexagonal nut up an asymmetric ramp, trying to keep the ring from falling off the ramp and advancing to the top of the ramp.

Various otologic surgery skill exercise modules 432 may require the use of two hands to manipulate beads and wires, simulating hand motions used in microscopic ear surgery.

Various otologic surgery skill exercise modules 432 using water or artificial blood to simulate bleeding requiring suctioning.

Various otologic surgery skill exercise modules 432 simulating the middle and inner ear structures, allowing for placement of stapes prostheses, ossicular replacement prostheses, and cochlear implants.

Various freestanding otologic surgery skill exercise module attachments received by the simulated small working port 440 on the housing 420 that contain a realistic ear canal, simulated tympanic membrane, or middle or inner ear structures. This would allow the practice of procedures such as ear tube placement, ear drum repair, removal of disease from the middle ear. See FIGS. 12A-C for images of a realistic ear canal for attachment to the small working port 440.

Various freestanding otologic surgery skill exercise module attachments made from CT scans of real temporal bones to facilitate pre-operative planning and patient-specific practice.

Placement of a realistic external ear made of silicone or other materials over top of the small working port 440 and/or the otologic surgery skill exercise module attachment 432 to simulate operating through a real external ear and ear canal.

Adaptation of the trainer 400 and exercise modules 432 to enable endoscopic sinus surgery skills training.

When the top housing 420 and the bottom housing 422 are attached together and a skill exercise module attachment 432 is attached to the platform 425, the interior of the simulated ear canal attachment 442 along with the interior of the top and bottom housings provides a suitable environment for practicing otologic surgery skills. The dimensions of the simulated ear canal working port attachment 442 and the distance of the skill exercise module attachment 432 from the small working port 440 allows a user to practice otologic surgical techniques under dimensional constraints such as those experienced when working on a patient. The depth of the skill exercise module 432 relative to the top of the small working port 440 is based on anatomical dimensions so as to provide a realistic hand to surgical subject working distance for otologic surgery including transcanal endoscopic or microscopic ear surgery. For example, the depth may be based on pediatric or adult anatomical data and instrument dimensions. The working distance of the trainer is configured such that when a user puts a surgical instrument into the trainer to perform an exercise the user will have the feeling of putting the instrument into a real ear. Typical working distances are on the order of 3 cm. Furthermore, diameter and/or volumetric shape of the simulated ear canal attachment 442 may be based on anatomical dimensions that simulate an ear canal. In this regard, the simulated ear canal attachment 442 and dimensions of the transcanal ear surgery training system 400 provide realistic working dimensions for inserting instruments into an external auditory canal and reaching features of interest in a middle ear or inner ear area.

Figure 5:
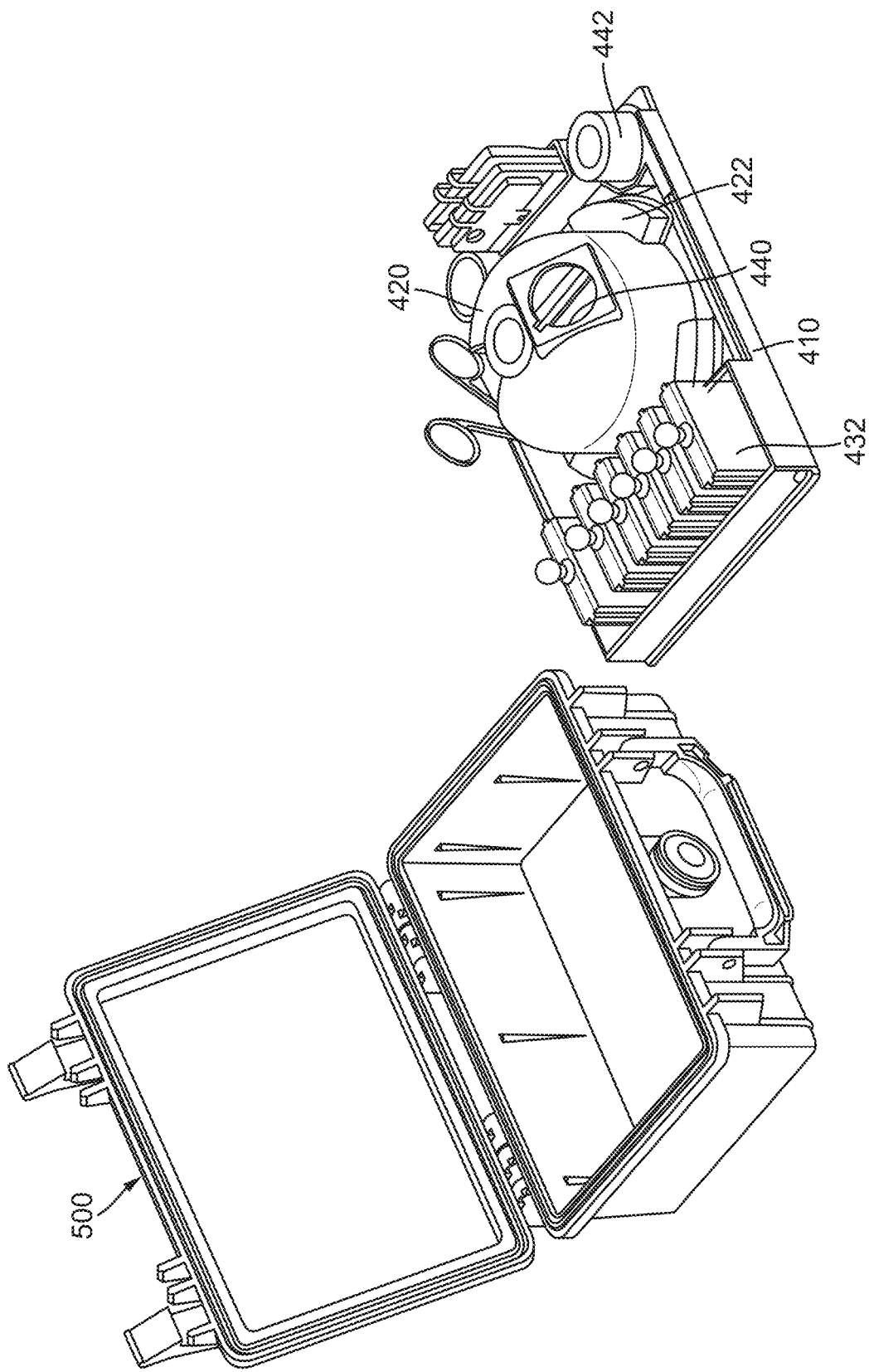
FIG. 5 illustrates an exemplary otologic surgery training system, according to some embodiments.

FIG. 5 illustrates an example of otologic surgery training system, according to some embodiments. Shown in FIG. 5 is the otologic surgery training system 400 including the top housing 420, the small working port 440, a simulated ear canal working port attachment 442, the base 410, the bottom housing 422, and the otologic surgery skill exercise module attachment 432. Also shown in FIG. 5 is a case 500 (or storage and organization system) that is configured to receive the otologic surgery training system 400. The storage and organization system includes the case and the series of racks to which the trainer housing attaches. The case 500 includes a handle for carrying the case 500 and a lid that opens and closes and latches to secure the lid in a close position. The case 500 is configured to secure in place the otologic surgery training system 400 and all the moving or separate parts or instruments of the otologic surgery training system 400 such that parts and instruments of the otologic surgery training system 400 stay in place when the case 500 is closed and held or carried by the handle.

Figure 6:
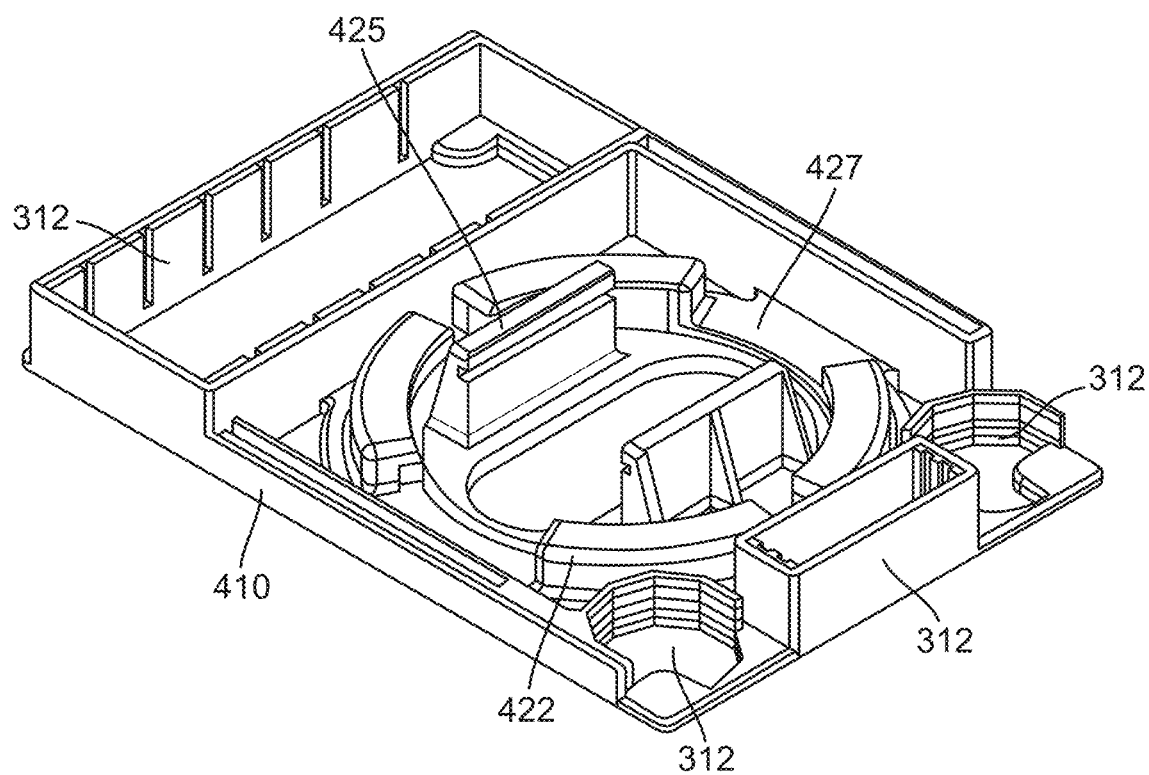
FIG. 6 illustrates a perspective view of a portion of the otologic surgery training system illustrated in FIG. 5, according to some embodiments.

FIG. 6 illustrates an example of a base of an otologic surgery training system including a bottom housing and an exercise module platform, according to some embodiments. Shown in FIG. 6 are the base 410, the bottom housing 422, the platform 425, the locking mechanism cutout 427, and the compartments or structures 312 to hold removable parts of the otologic surgery training system 400 or instruments utilized during otologic surgery exercises.

Figure 7:
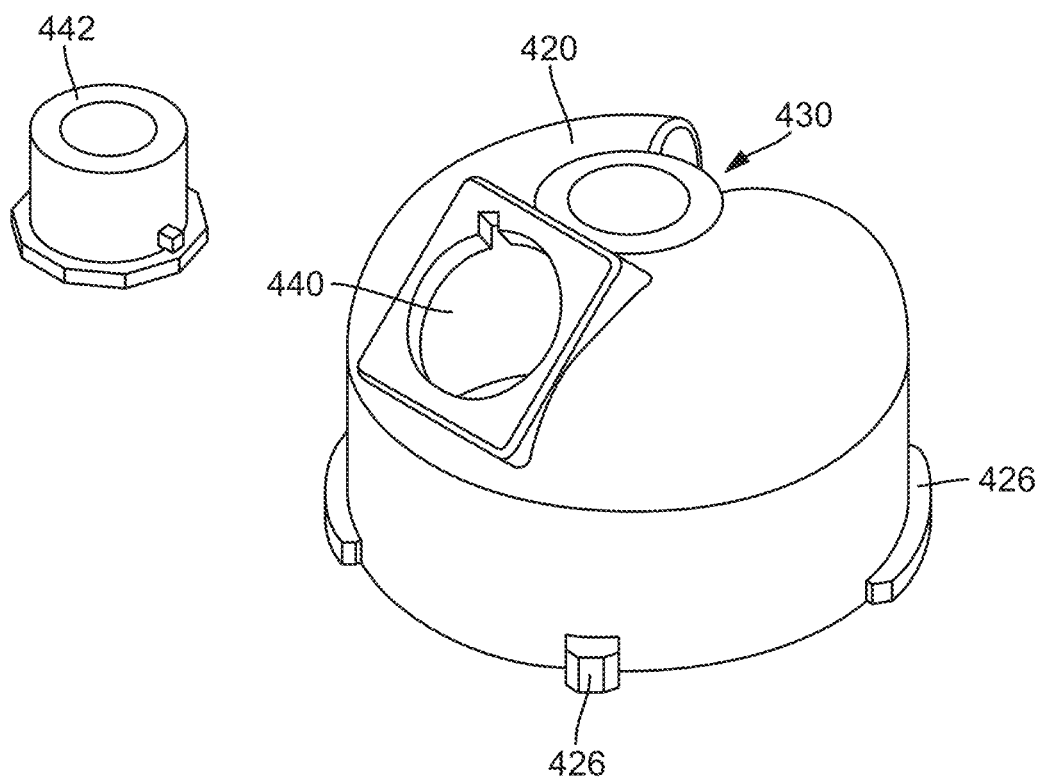
FIG. 7 illustrates a top housing and a simulated ear canal working port attachment of the otologic surgery training system illustrated in FIG. 5.
Figure 8A:
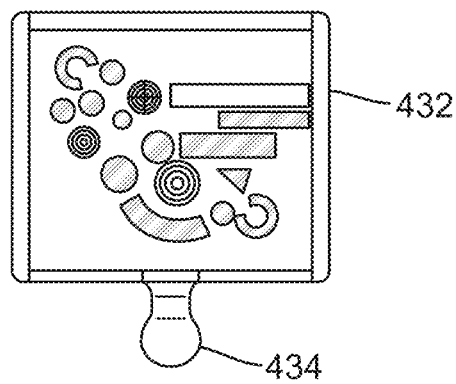
FIGS. 8A-8F illustrate a plurality of exemplary otologic surgical skills exercise modules, according to some embodiments.
Figure 8B:
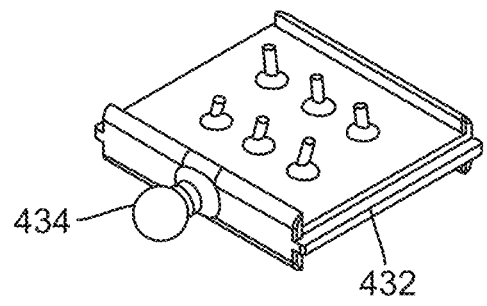
Figure 8C:
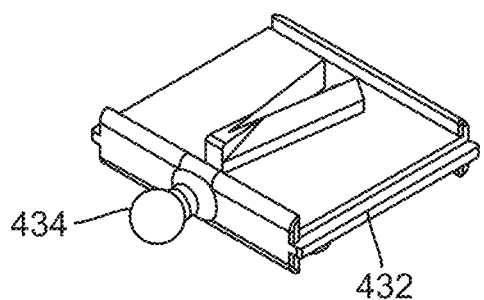
Figure 8D:
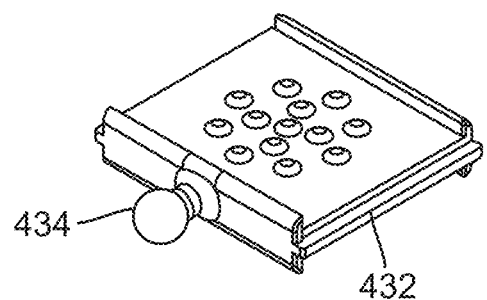
Figure 8E:
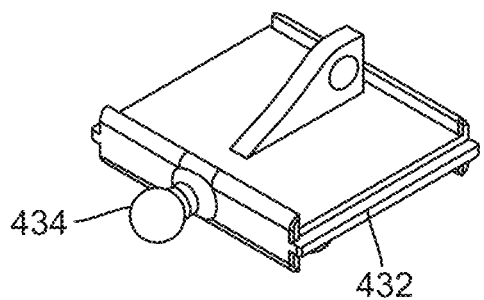
Figure 8F:
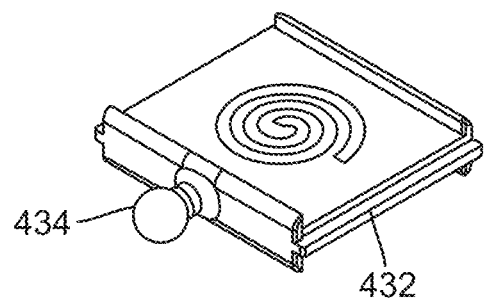

FIG. 7 illustrates a top housing and a simulated ear canal working port attachment, according to some embodiments. Shown in FIG. 7 are the top housing 420, the large working port 430, the small working port 440, the simulated ear canal working port attachment 442, and the locking mechanism tabs and/or rails 426.

FIGS. 8A-8F illustrate a plurality of examples of otologic surgical skills exercise modules, in accordance with various embodiments. Shown in FIGS. 8A-8F are variations of the exercise module attachment 432. In some embodiments, the exercise module 432 includes a tab or handle 434 for a user to hold the module or maneuver the base of the exercise module attachment 432 when attaching the base to the platform 425.

Figure 9A:
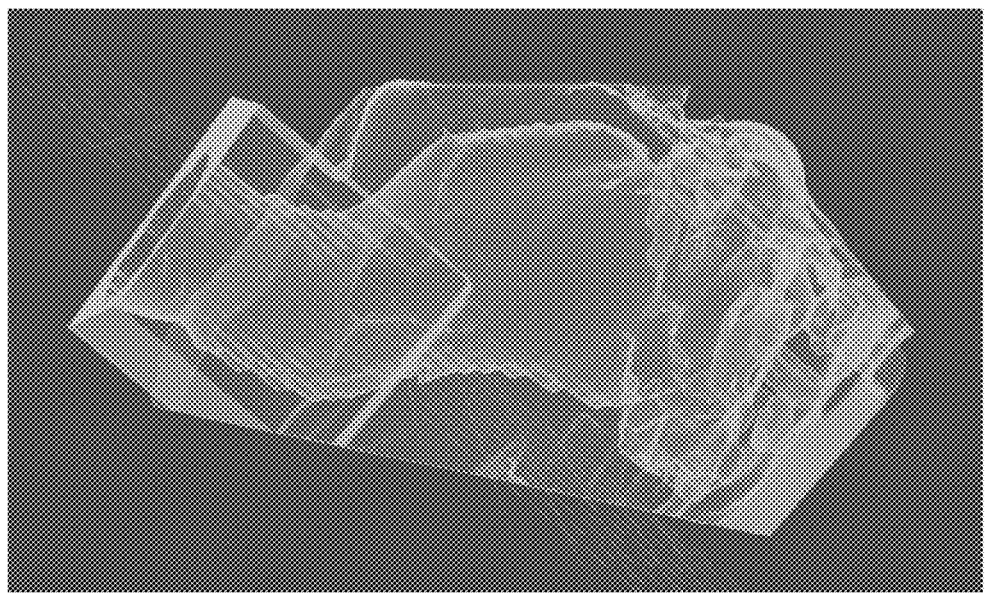
FIGS. 9A-9B illustrate computer models of an adult external auditory canal and middle ear for 3D printing of training modules for a transcanal ear surgery training device, according to some embodiments.
Figure 9B:
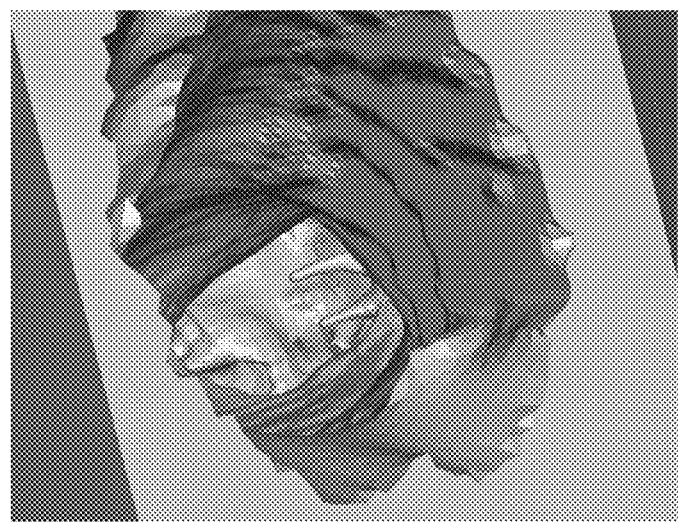
Figure 12A:
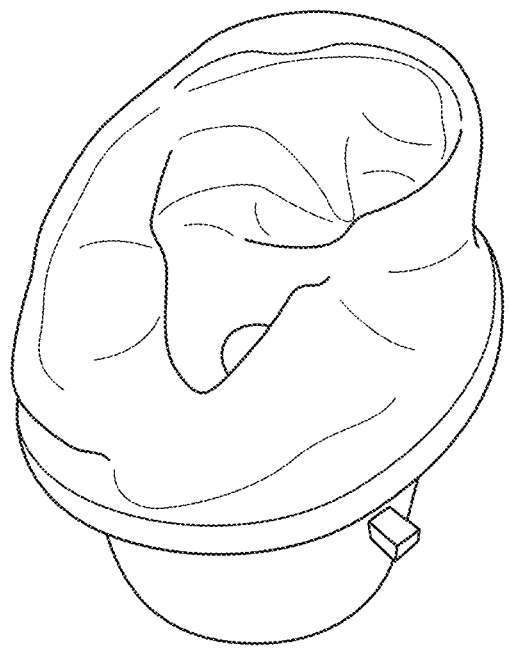
FIGS. 12A-12C illustrate an anatomical ear canal working port attachment of the otologic surgery training system.
Figure 12B:
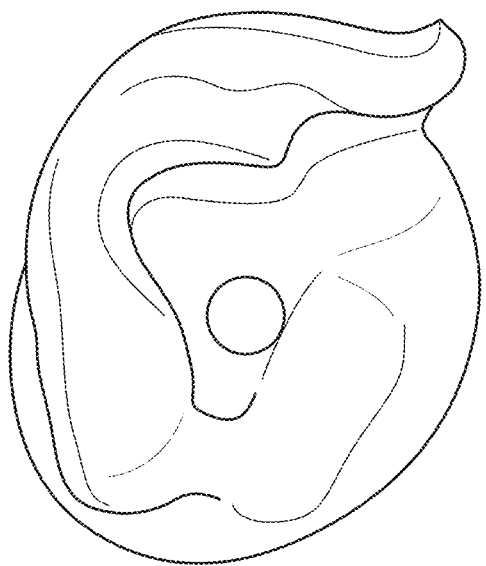
Figure 12C:
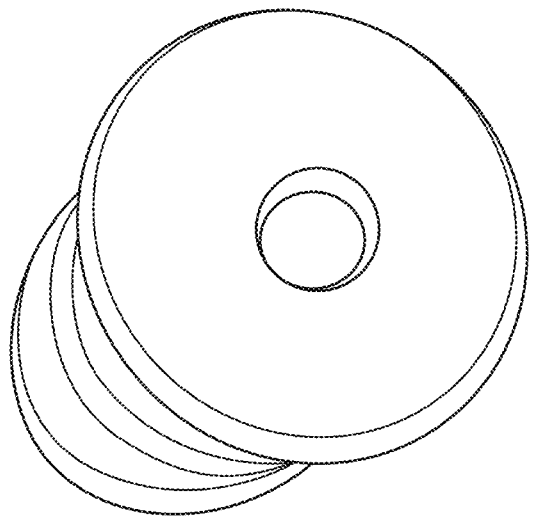

FIGS. 9A-9B illustrate computer models of an adult external auditory canal and middle ear based on a computerized axial tomography (CT) scan. Computer models based on a CT scan such as those shown in FIGS. 9A-9B may be utilized for 3D printing a simulated ear canal attachment 442 or a stand-alone simulated ear canal attachment 442 to form a more realistic ear canal and middle ear environment. With reference to FIGS. 12A-C, an anatomical ear canal port (as the attachment 442) could be 3D modeled and printed based on imported MRIs, CT scans, etc. from a patient. The entire outer ear, ear canal, and tympanic membrane geometry could be recreated. Moreover, this would be 3D printed or injection molded using a rubber-like material simulating tissue. To allow for multiple uses, the tympanic membrane could be designed as a removable cartridge. As noted above, this allows for simulation of vent tube insertion, using tympanoseal to treat a perforation, or tympanomeatal flap incisions to access the middle ear. The ear canal attachment could also deform and reform similar to an in vivo experience.

In some embodiments, the transcanal ear surgery training system includes an electronic feedback system. For example, the training system may include an optical tracking system for measurement and tracking of instrument positions in three dimensions during otologic surgical skill exercises. For example, endoscopes used to perform the otologic surgical exercises may be equipped with illumination elements and 3D stereo camera elements that are communicatively coupled to a computer system via a wireless or wired connection. The optical tracking system may be utilized for navigation and/or monitoring of the endoscope movements. For example, the optical tracking system may be utilized to provide automated performance feedback assessments of a user's skill exercises. Other types of automated feedback systems may be built into or attached within the transcanal ear surgery training system, for example, in the system housing, the simulated ear canal attachment 442, the otologic surgery skill exercise module attachment 432, or the stand-alone otologic surgical skills exercise module. The automated feedback systems may include alarms that indicate when a structure is touched or a barrier is crossed. For example, pressure sensitive platforms in the feedback systems may sense force applied by surgical instruments during surgery exercises and provide feedback data on forces sensed in various points within the ear surgery training system. In some embodiments, a camera may be disposed within the top housing 420 and/or the bottom housing 422 for recording exercise performance. The automated feedback systems are communicatively coupled to a computer system via a wireless or wired connection and report feedback data to the computer system. In some embodiments, the transcanal ear surgery training system 400 includes an electronic processor, memory, and display device. The electronic processor may receive data from the feedback system of the transcanal ear surgery training system, and may display automated performance feedback assessments of a user's skill exercises from the feedback system for users based on their surgery skills exercise performance.

Figure 10:
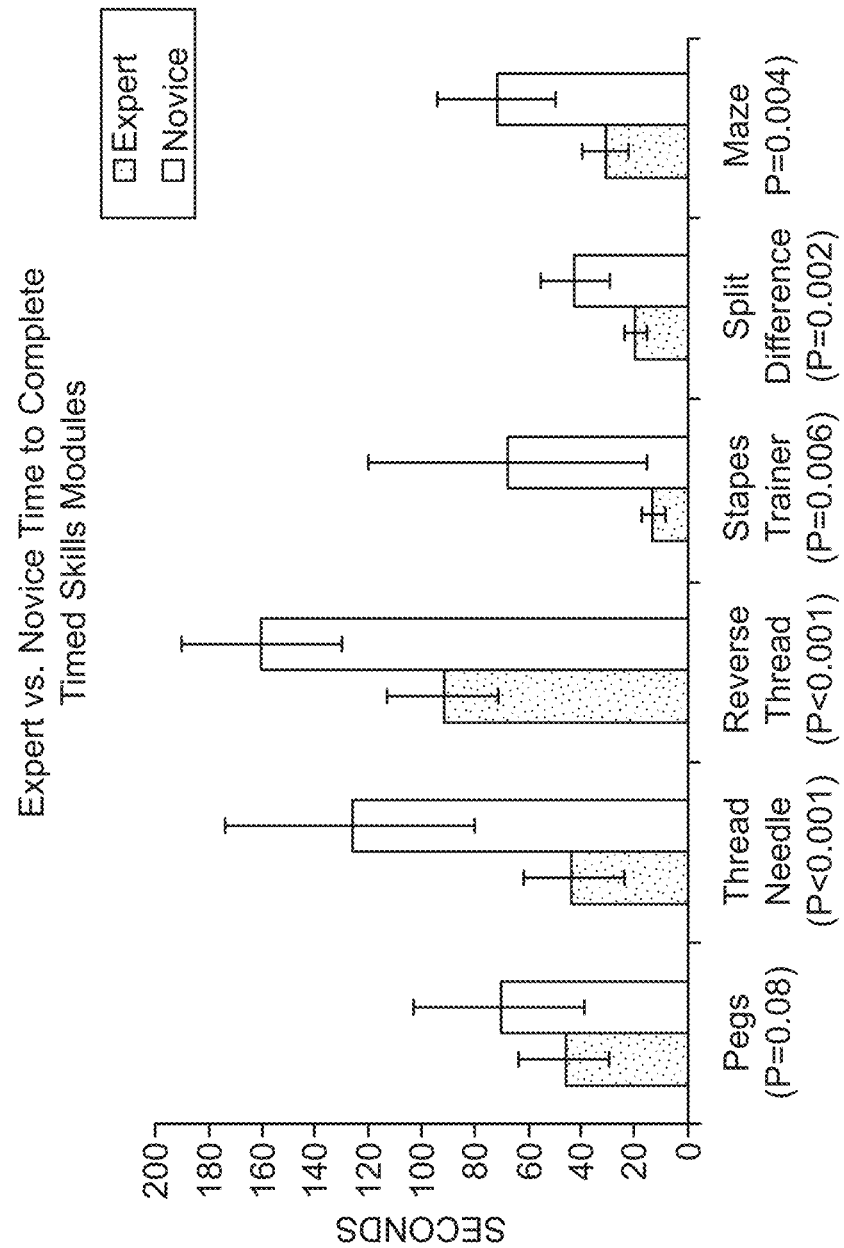
FIG. 10 graphically illustrates the results of a time based transcanal ear surgery training device skills performance study comparing expert versus novice surgeons utilizing a handmade transcanal ear surgery trainer.
Figure 11:
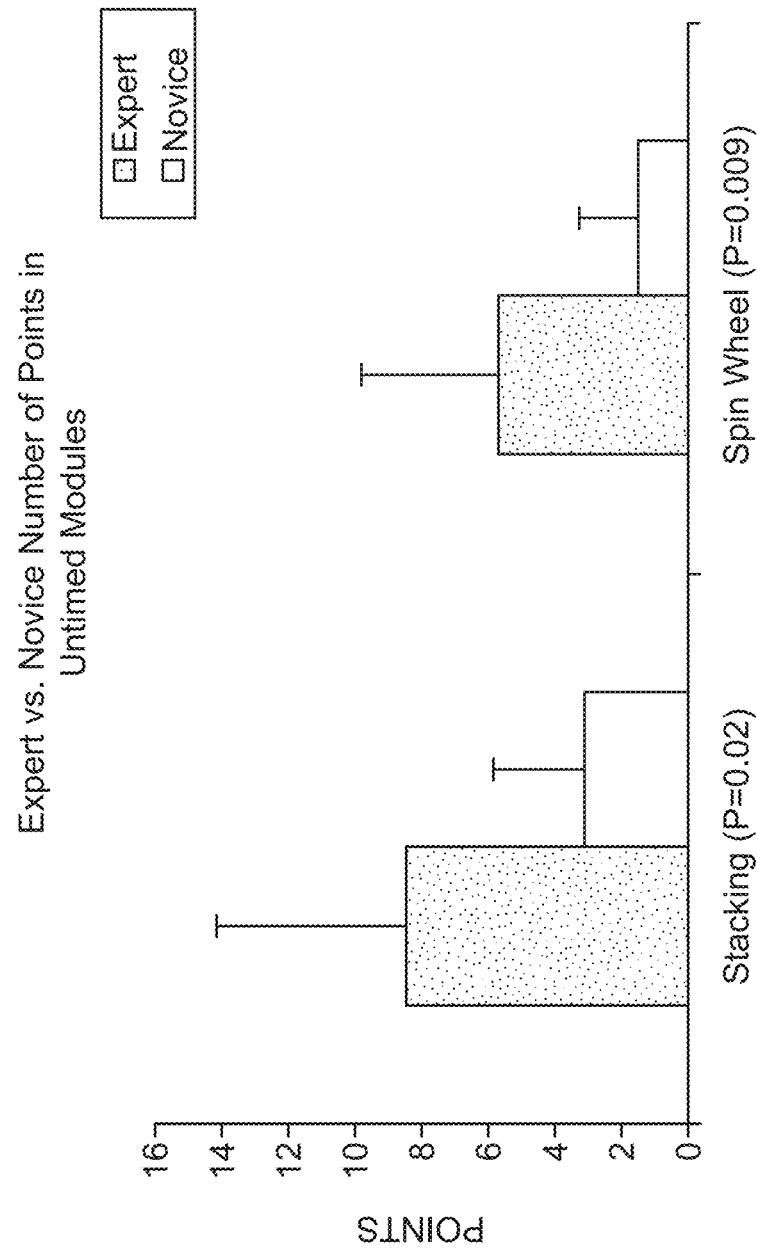
FIG. 11 graphically illustrates the results of a points based otologic surgery training device skills performance study comparing expert versus novice surgeons utilizing a handmade otologic surgery trainer.

FIGS. 10-11 illustrate the results of a time based and an untimed point based transcanal ear surgery training device skills performance study comparing expert versus novice surgeons utilizing a handmade transcanal ear surgery trainer. In order to determine whether a transcanal ear surgery trainer can differentiate between expert and novice performance, and is therefore a useful training tool, a pilot validation study was performed. A handmade trainer and skills modules was utilized with seven participants ranging in experience from medical students to expert otologic surgeons. The group was divided into "novices" who perform less than ten endoscopic procedures annually (n=4) and "experts" who perform greater than ten endoscopic procedures annually (n=3). Each participant completed eight skills modules in duplicate or triplicate, and the modules were scored according to time or points, depending on the module. Each participant also completed a Likert-based post-simulation survey. Expert performance was significantly superior to novices in 100% (8/8) of skills modules, i.e. threading beads on a wire (43 vs. 27 seconds, $p<0.001$) and placing a simulated prosthesis (13 vs. 68 seconds, $p=0.006$).

Most participants (86%) agreed the skills trainer orientation was accurate and all participants (100%) were satisfied with the experience. Although this was a small validation study using a prototype, the results indicate that these simple modules are testing important surgical skills and will be a useful component of a comprehensive otologic surgery training program.

TABLE 1

Scoring protocols and difficulty levels for endoscopic ear surgery skills modules.

| Skill Module | Scoring Protocol | Reported Mean Difficulty: 1 (Easiest) to 5 (Hardest) |
|---|---|---|
| Pegs and rings | Time to transfer three rings to second row of pegs and back again using a cup forceps. | 3 |
| Thread the needle | Time to place a single bead on each of the three wires using an alligator forceps. | 3.7 |
| Reverse thread the needle | Time to place five simulated prostheses into beads via the simulated ear canal. Maximum time is 180 seconds. | 3.3 |
| Prosthesis placement | Time to successfully place a single prosthesis via the simulated ear canal. Maximum time is 150 seconds. | 3 |
| Precision stacking | One point awarded for a stack of two, three points for stack of three, and five points for stack of four. Points are additive per each trial, which consists of the chance to stack seven nuts. | 4.3 |
| Spin the wheel | One point for each revolution of a nut spun on the platform using a Rosen needle. Points are additive and three nuts are spun per trial. | 4.3 |
| Split the difference | Time to push washer on wires until it reaches end and falls successfully onto vertical wire. If the washer falls off, a time of 60 seconds is recorded. | 2 |
| The maze | Time to navigate a bead through the maze. If the bead falls off or into a hole, a time of 90 seconds is recorded. | 1.8 |

Participants of the study were surveyed about the subjective difficulty level of each skills exercise. Table 1 includes results of the survey. While some of the exercises with higher reported difficulty were observed to have larger gaps in expert versus novice time, there was not an established trend. The range of reported exercise difficulty was 1.8 to 4.3 on a scale from 1 to 5, indicating that easier as well as more challenging exercises were developed and tested in this study.

Although the invention has been described in detail with reference to certain preferred embodiments, variations and modifications exist within the scope and spirit of one or more independent aspects of the invention as described. Various features and advantages of the invention are set forth in the following claims and in the accompanying drawings.

What is claimed is:

1. A system for otologic surgical skills training, the system comprising:
   a housing;
   a first working port extending through the housing, the first working port configured to receive an otologic surgical instrument;
   a simulated ear canal removably attachable to the first working port; and
   an otologic surgery skill exercise module positioned inside the housing, wherein the otologic surgical instrument is configured for performing otologic surgery exercises on the otologic surgery skill exercise module, and
   wherein the simulated ear canal includes a simulated ear canal working port in communication with the first working port, the simulated ear canal working port having a diameter configured for simulating transcanal ear surgery, and
   wherein the housing includes a second working port that is larger than the simulated ear canal working port for passage of otologic surgical instruments to the otologic surgical skills exercise module for conducting otologic surgical exercises with less spatial constraints than the simulated ear canal working port.

2. The system of claim 1, wherein the housing comprises a top housing that includes the simulated ear canal and a bottom housing that is removably attachable to the top housing.

3. The system of claim 1, wherein at least one of the housing, the simulated ear canal, and the otologic surgery skill exercise module are manufactured by a 3D printing process.

4. The system of claim 1, wherein the simulated ear canal is interchangeable with other removably attachable simulated anatomical parts.

5. The system of claim 1, wherein the simulated ear canal is interchangeable with different types or sizes of simulated ear canals.

6. The system of claim 1, wherein the first working port is configured to secure the simulated ear canal to the housing.

7. The system of claim 1, wherein the simulated ear canal is a self-contained working port comprising the otologic surgery skill exercise module.

8. The system of claim 1, wherein the simulated ear canal is modeled based on anatomical data of an external auditory canal and middle ear.

9. The system of claim 1, wherein an interior of the housing includes a fixed platform that is configured to removably receive the otologic surgery skill exercise module.

10. The system of claim 1, wherein the otologic surgery skill exercise module is positioned a working distance from the housing for simulating an anatomically correct otologic surgery working environment.

11. The system of claim 1, wherein the otologic surgery skill exercise module includes subcentimeter or sub-millimeter scaled features for practicing otologic surgical skills.

12. The system of claim 1, wherein the otologic surgery skill exercise module includes features for practicing otologic surgical skills including placing rings on pegs, stacking objects, placing beads onto a wire, or navigating a maze with a bead utilizing the otologic surgical instrument.

13. The system of claim 1, wherein the otologic surgical instrument comprises an endoscope or a microscope otologic surgical instrument.

14. The system of claim 1, further comprising an electronic feedback system for sensing and communicating user performance, the electronic feedback system including one of an optical sensor, a force sensor, and a camera.

15. The system of claim 2, wherein the top housing includes tab extensions and the bottom housing includes cutouts for vertically receiving the tab extensions of the top housing and the bottom housing includes a groove for rotationally receiving the tab extensions of the top housing.

* * * * *